United States Patent [19]   [11] Patent Number: 6,118,846
Liu                               [45] Date of Patent: Sep. 12, 2000

[54] BAD PIXEL COLUMN PROCESSING IN A RADIATION DETECTION PANEL

[75] Inventor: Chuande Liu, Hockessin, Del.

[73] Assignee: Direct Radiography Corp., Newark, Del.

[21] Appl. No.: 09/255,772

[22] Filed: Feb. 23, 1999

[51] Int. Cl.[7] .................................................. G01N 23/04
[52] U.S. Cl. ............................. 378/62; 378/98; 378/98.8
[58] Field of Search ............................. 378/62, 98, 98.2, 378/98.8; 382/128, 131, 132

[56] References Cited

U.S. PATENT DOCUMENTS

| | | | |
|---|---|---|---|
| 3,830,972 | 8/1974 | McHugh et al. | 178/7.1 |
| 4,178,510 | 12/1979 | Wagner | 250/445 T |
| 4,567,525 | 1/1986 | Endo et al. | 358/213 |
| 4,589,028 | 5/1986 | Ochi | 358/213 |
| 4,602,291 | 7/1986 | Temes | 358/221 |
| 4,694,342 | 9/1987 | Klees | 358/167 |
| 5,047,863 | 9/1991 | Pape et al. | 358/213.16 |
| 5,499,114 | 3/1996 | Compton | 358/483 |
| 5,748,768 | 5/1998 | Sivers et al. | 382/130 |
| 5,832,055 | 11/1998 | Dewaele | 378/62 |

Primary Examiner—David V. Bruce
Attorney, Agent, or Firm—Ratner & Prestia

[57] ABSTRACT

A process and associated apparatus for performing defective pixel correction in a radiation detector having a plurality of radiation sensors arrayed in rows and columns. The process and associated apparatus are specifically directed to correcting defects consisting of a plurality of adjacent pixels arrayed along and connected to a common electrode forming a bad pixel line. The pixel correction is accomplished by identifying the bad pixel line, forming a window of a plurality of pixel lines co-extending along the bad pixel line; identifying a limited number of adjacent pixel lines adjacent to the bad pixel line as also being bad pixel lines; preferably subdividing the window pixels into smaller windows along the bad pixel line, deriving correction coefficients for all bad line pixels in each subdivision from the good pixels in each subdivision and using the correction coefficients to correct the pixels in both the original bad line and in the adjacent bad pixel lines.

18 Claims, 2 Drawing Sheets

BAD PIXEL COLUMN PROCESSING IN A RADIATION DETECTION PANEL

BACKGROUND OF THE INVENTION

1. Field of the Invention

This invention relates to digital radiographic systems and more particularly to a process for correcting digital image values from a defective pixel column.

2. Description of Related Art

In the past decade there has been great progress made in the area of direct radiographic imaging using detectors comprising a two dimensional array of minute sensors to capture a radiation generated image. Information representing an image is captured, often as a charge distribution stored in a plurality of charge storage capacitors in individual sensors arrayed in a two dimensional matrix. We will refer to such detectors generically as direct radiographic detectors, or simply as detectors, to differentiate them from the often referred to traditional radiographic detectors which employ a photosensitive film usually in combination with an intensifying screen to produce a photographic image of the incident X-ray radiation.

The direct radiographic detectors typically comprise a two dimensional array of sensors with associated switching and addressing circuitry built on an insulating substrate, usually a glass plate. U.S. Pat. No. 5,319,206 issued to Lee et al. on Jun. 7, 1997, shows a typical direct radiation detector comprising an array of sensors for the generation and capture of charges following exposure to X-ray radiation. Readout of the stored charges is accomplished in any one of a plurality of manners. U.S. Pat. No. 5,648,660, also by Lee et al. discloses a method for the readout of stored charges in a direct radiographic imaging panel.

Direct radiation detectors offer a number of distinct advantages over the traditional film methods. The availability of a radiogram in electronic signal format, permits the use of digital signal conversion and all the advantages of signal storing, retrieval, transmission and processing associated with digital imaging.

Direct radiation detectors, however, are not free of problems uniquely associated with them. Practical diagnostic quality and size detectors require panels comprising millions of individual sensors arrayed in rows and columns. Typically, such sensors are scanned to obtain the electrical signal stored therein which represents the radiogram. Scanning is accomplished through a process that uses a plurality of access switches associated with the individual detectors. Switching is usually done with an FET transistor by addressing its gate and the signal is recovered through a source line connected to the FET source electrode.

Any defective sensor or line will result in loss or distortion of the signal from the sensor or from a plurality of sensors, resulting in what is commonly referred to as Bad pixel error. Bad pixel errors produce image artifacts which interfere with the ability to properly read the radiogram and may produce false readings.

There are presently a number of ways known to identify and compensate for the presence of bad pixels in imaging panels comprising a plurality of sensors. It is known for instance to obtain a flat field exposure of the detector (that is a uniform intensity exposure) and read out the resulting image. In a perfect detector, the signal output level from each sensor would be exactly the same. In reality, the output varies somewhat from sensor to sensor. Variations within acceptable limits are devised and sensors whose output falls outside predetermined acceptable limits are defined as "bad" pixels. These bad pixels are typically mapped and their output replaced by a calculated value computed by interpolation from a plurality of neighboring pixels. Variations in the output of the acceptable pixels are compensated by a pixel gain adjustment for each sensor so that the final output is substantially uniform for the flat field exposure.

While the above approach to solving the bad pixel problem is useful in correcting individual bad pixels, there is another type of problem that remains unsolved. At times there is a column of a plurality of sensors all connected to the same source addressing conductor (line) that is defective. When this occurs, it has been observed that the output of a number of adjacent sensor columns is also effected, and, furthermore, that the effect on the adjacent sensors is not linear with exposure. (Exposure is the product of the radiation intensity incident on the detector multiplied by the time the radiation impacts the detector.)

This problem produces undesirable and unpredictable artifacts which cannot be adequately corrected by the known methods. There is, therefore need to provide a method for correcting such bad pixel column defects.

SUMMARY OF THE INVENTION

It is an object of this invention to provide a method for correcting inaccurate pixel values resulting from a defective column of radiation sensors in a radiation detecting array of sensors. The first step in implementing this method includes identifying the location of the bad sensors forming the bad pixel column of pixels and storing this location in a memory.

Once this location has been identified, following imaging exposure of the detector, the process comprises selecting a plurality of adjacent co-extensive columns of pixels, on either side of the bad pixel column of sensors and storing the values of each pixel and the values of the pixels in the bad pixel column to form an array of selected first pixel values. Because a bad pixel column has been observed to effect a number of adjacent columns, a preset number of adjacent columns are also treated as defective.

A mean column value for each column of pixel values in each column is then calculated. Ignoring the bad pixel column or columns mean value, a set of base line values for each column in each sub-array (except for the defective pixel column) is calculated, preferably using least mean square approximation to fit the mean column values into a first order polynomial.

Using the first order polynomial, baseline values for the omitted bad pixel columns are next derived for each column, including the previously omitted bad pixel column or columns. The ratio of the mean pixel values in the bad pixel columns to the base line values for the bad pixel columns produces a distortion coefficient for each of the bad pixel columns. This distortion coefficient is applied to the individual pixel values in each corresponding bad pixel column to obtain a corrected pixel value which replaces the defective pixel value.

The accuracy of this correction method is greatly enhanced by subdividing the array of selected first pixel values into a plurality of smaller sub-arrays along the columns, each sub-array encompassing only a few rows, and preferably having the sub-arrays overlap. The above process is then applied to each sub-array of pixel values rather than to the full array of values.

Further accuracy enhancement may be achieved by deriving an approximation indicator for each of the sub-arrays. This indicator is related to the deviation of the mean values from the baseline and is a measure of the accuracy of the distortion coefficient calculation. The accuracy indicators are then divided into a lower first half group and a higher second half group, based on their value. All sub-arrays having an accuracy indicator in the second half are identified and the distortion coefficients for these arrays are replaced by new distortion coefficients extrapolated from the distortion coefficients of adjacent sub-arrays.

BRIEF DESCRIPTION OF THE DRAWINGS

The invention can be more fully understood from the following description thereof in connection with the accompanying drawings described as follows.

DESCRIPTION OF THE PREFERRED EMBODIMENT(S)

Throughout the following detailed description, similar reference characters refer to similar elements in all figures of the drawings.

The invention will next be described with reference to a detector which can be any radiographic detector capable of generating an electrical signal representing impinging radiation intensity variations. Such radiographic detectors are described inter alia in U.S. Pat. No. 5,773,832, issued Jun. 30, 1998 to Sayed et al., U.S. Pat. No. 5,254,480, issued Oct. 19, 1993 to Nang T. Tran, or U.S. Pat. No. 5,315,101, issued May 24, 1994 to Hughes et al.

A preferred detector contemplated for use in the present invention is a direct radiation conversion detector of the type disclosed in the aforementioned U.S. Pat. No. 5,648,660 by Lee et al. As disclosed in this patent the detector comprises a two dimensional array of individual radiation sensors on a supporting dielectric base forming a panel of appropriate size, usually 14 by 17 inches. The panel is enclosed in a light tight enclosure such as disclosed in U.S. Pat. No. 5,804,832 issued to Crowell et al. Each of the sensors comprises a charge storage capacitor and a switching transistor adjacent the capacitor. Conductive lines extend in the spaces between sensors for actuating the switching transistor and retrieving the electrical signed stored in the capacitor. The transistor is typically an FET whose source and gate electrodes are connected to conductive lines running along individual columns and rows.

A photoconductive layer is placed over the individual sensors and a biasing electrode is placed over the photoconductive layer. Charge blocking layers may be placed on one or both sides of the photoconductive layer. Upon exposure to radiation, electron and hole pairs are freed in the photoconductive layer. Under an imposed static electric field, electrons migrate to the biasing electrode and holes migrate to the charge storage capacitor (depending on the polarity of the applied field).

Following exposure, the biasing field is removed and the accumulated charge in the individual sensors is read out, amplified, digitized and stored. The detector is reconditioned for the next exposure by exposing to illuminating radiation as disclosed in U.S. Pat. No. 5,563,421 issued to Lee et al. Preferably, between exposures, the detector is continuously cycled between a state where the biasing voltage is zero and a state where a biasing voltage other than zero is applied to the biasing electrode followed by image readout even when no exposure has occurred. This is referred to as the standby state, as distinguished from the ready state in which the cycling has been interrupted and a proper biasing voltage has been applied to the sensors. U.S. patent application Ser. No. 08/979,134 describes this process in detail.

The charge obtained from the sensors and digitized represents the raw data output of the detector. The output of each sensor corresponds to one picture element (PIXEL) of the image. This raw digital data is subjected to a first gain equalization process and then to a bad pixel correction process. Typically, gain equalization involves applying a pre-calculated gain factor, usually stored as a look up table (LUT) to each pixel value to compensate for gain non uniformity in the individual sensors. The bad pixel correction follows and entails the replacement of previously mapped bad pixels by a value calculated by averaging 8 adjacent pixel values from the immediate surrounding pixels. The resulting image data is saved for further processing according to this invention.

This invention corrects defects typically associated with pixels aligned in the direction of a conductive line connecting the source of the switching transistors of a plurality of pixels. However the invention is equally applicable to correct defects associated with pixels aligned along a conductive line connecting the gates of the switching transistors which are usually orthogonal to the source lines. In order to simplify the description of this invention we will refer to a defective plurality of pixels connected to a common conductive line as a bad pixel column regardless of whether the common conductive line connects the switching transistor source or the transistor gates or whether it is along a row or a column of the detector.

In implementing this invention, following manufacturing and assembly of a detector, the detector is subjected to a flat field exposure and the location of any bad pixel columns is identified. A bad pixel column contains a plurality of adjacent pixels arrayed along a common connecting conductor, and comprises preferably nine adjacent pixels or more, whose output is outside a predetermined acceptable level for the given exposure. Typically, bad pixel column defects appear as a no signal (black) line or a saturation signal line (white). In the following description of this invention, using a two dimensional array of mutually perpendicularly arrayed sensors, we adopt the following terminology: pixels arrayed along the conductive lines connected to the source electrode of the switching FETs are referred to as forming a column. Pixels arrayed perpendicular to columns form rows. A pixel location is identified by its row and column as $R_xC_y$.

Figure 1:
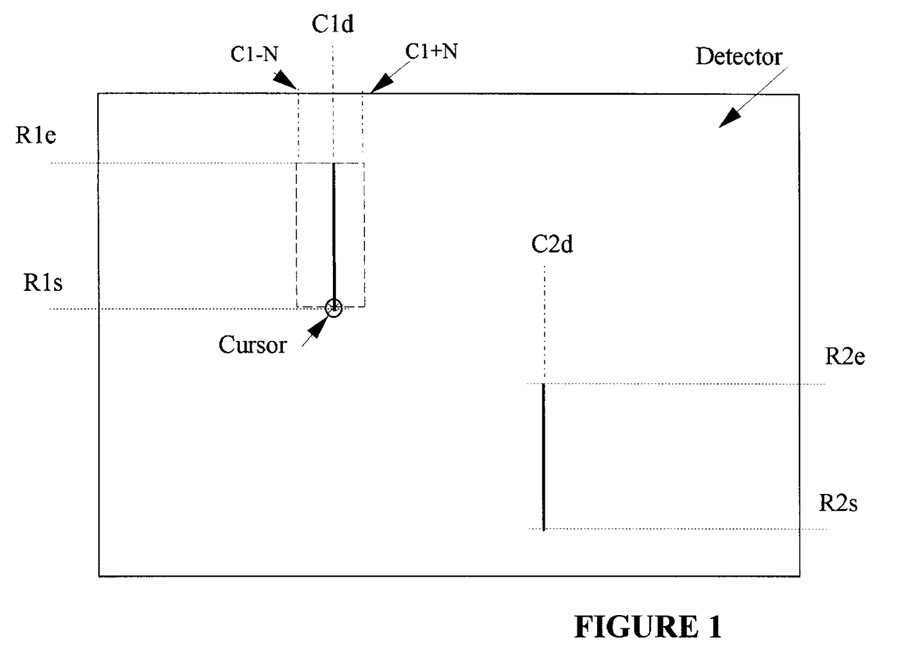
FIG. 1 shows an interactive radiographic examination system in accordance with this invention.

The flat exposure image is displayed on a display screen of, for instance, a computer display screen. FIG. 1 is a schematic representation of such display from a radiation detection panel following a uniform radiation exposure of the detection panel. The display has a uniform gray appearance except for the two black vertical lines shown. These represent two bad pixel columns C1 and C2. Zooming in and out display function permit to display magnified portions of the detector output. Using a calibrated cursor, calibrated so that its position on the display corresponds to the rows and columns of the detector sensors, the co-ordinates in terms of row and column of the starting point R1s and ending point R1e as well as the bad pixel column C1 are identified by placing the cursor at the start and at the end of the black line. The technology required for this process is similar to the technology used in tracking the location of a mouse controlled cursor on a computer display screen and does not require any further elaboration. Once the first bad pixel column has been mapped, the next bad pixel column C2 is identified and its co-ordinates stored, and so on until all bad pixel columns have been identified and their co-ordinates stored in a bad pixel column file. Preferably, the display used to identify the bad pixel columns is done using the raw data obtained from the detector prior to any image processing.

A bad pixel column is mapped by its starting coordinated, x1s, y1s, and ending coordinated, x1e, y1e; x2s, y2s, and x2e, y2e, etc. which are stored in the bad pixel column file The bad pixel column correction processing routine uses the location information provided by the bad pixel column file to process one pixel column at a time.

Following the radiographic exposure of the detector, the detector output is amplified and converted into digital values. These values first undergo a gain correction process whereby each individual sensor output is adjusted based on a pre-calculated gain factor to obtain gain corrected digital values. Gain correction is well known and commonly used in this type of detector to compensate for unequal response characteristics of the plurality of sensors in the detector. Next the data undergoes a bad pixel correction. This is also well known in the art and typically involves mapping each defective pixel and replacing each defective pixel value by a value calculated from the surrounding pixels.

This corrected raw data is next used to accomplish a further correction of the pixel values in the bad pixel column and in columns around the bad pixel column, which tend to be effected by the bad pixel column problem.

Because of the nonlinear characteristics of the bad pixel column type defect with exposure, one may not correct for this type of defect using data from a single intensity level flat field exposure of the detector. The process according to this invention calculates new distortion coefficients (D) after each imaging exposure using the actual exposure data after it has been corrected for gain non-uniformity and for bad pixels.

Figure 2:
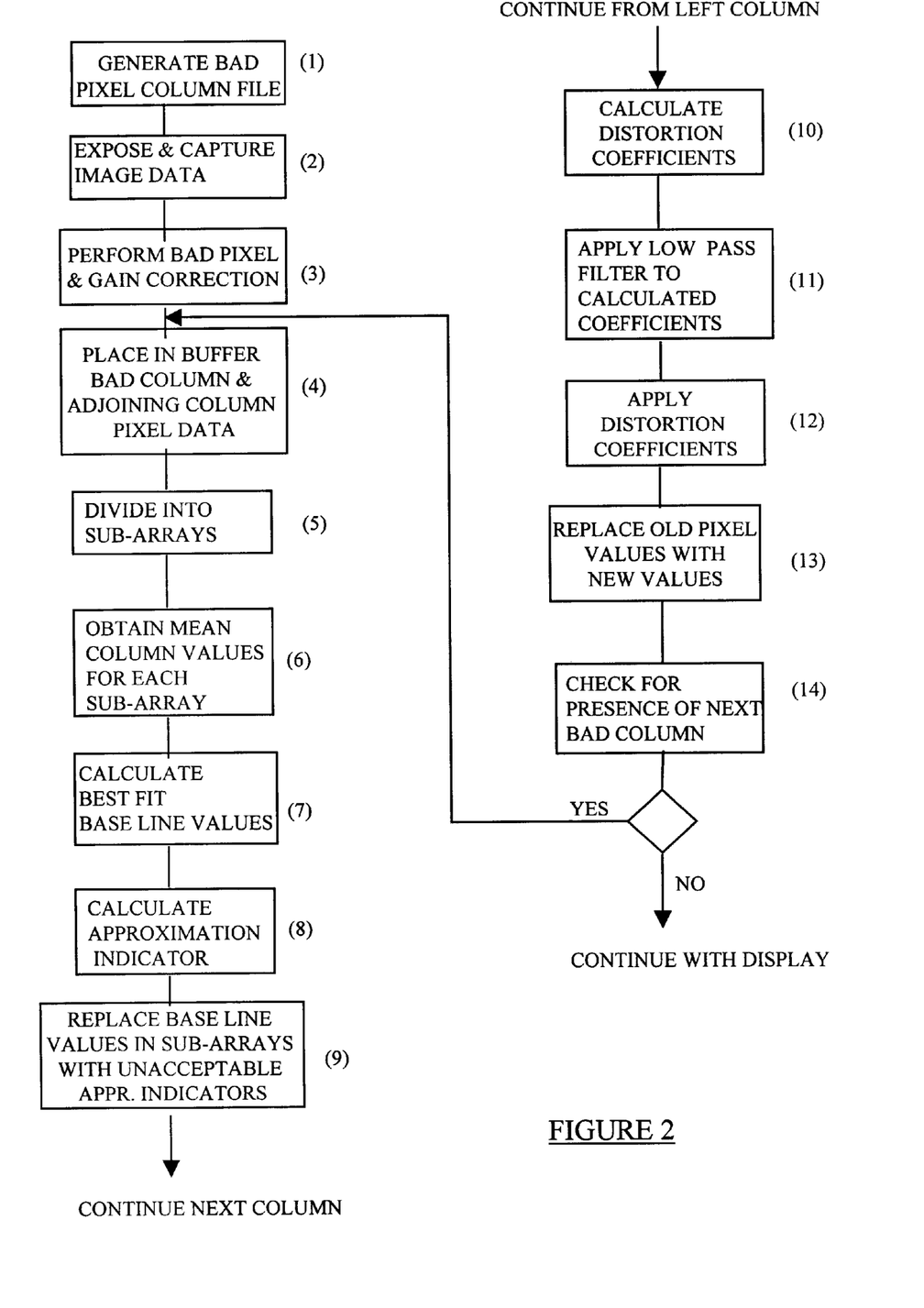
FIG. 2 shows a flow diagram of the steps performed by the system in implementing the present invention.

FIG. 2 shows a flow diagram of the steps to accomplish this correction according to the present invention.

As explained above, the first step is the identification of the bad pixel columns and the creation of a bad pixel column map (1) which contains the bad pixel columns for a detector. Once this file is created, it is quickly available for identifying and processing pixels.

Once the image is captured (2), gain calibration and pixel correction is performed (3). The process next involves capturing in a buffer the pixel values for a predetermined number N of columns $C1_N$ on either side of the bad pixel column to form an array of pixel values corresponding to rows R1s to R1e and columns $C1_{-N}$ to $C1_{+N}$, which is stored in a buffer memory (4). Preferably, N=16 provides a good database for the ensuing calculations, and results in commercially satisfactory corrections.

The buffered array is next subdivided into sub-arrays or blocks of data (5), extending from −N to +N and only a few rows, usually between 4 and 8, even though other numbers may be used. Preferably, the sub-arrays are overlapping, that is they have one or two rows in common with the adjacent sub-array.

Figure 3:
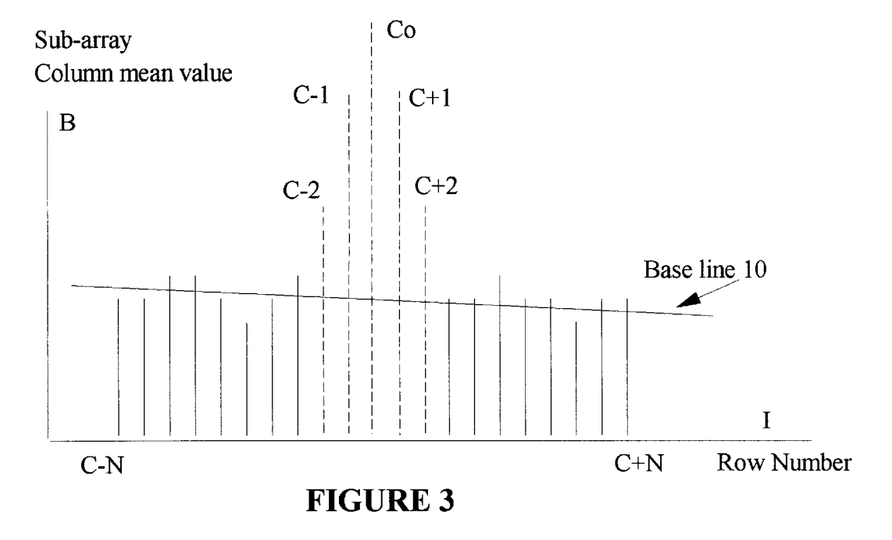
FIG. 3 shows a graphic representation of the calculation of the baseline.

Beginning with a first sub-array, i.e. the sub-array containing R1s, an average pixel value is calculated for each column in the sub-array, to form a row of mean values (6). FIG. 3 graphically represents this process for a case where N=10. As illustrated in FIG. 3, the y axis corresponds to the mean of the digital values for a column of this sub-array. Once the mean values have been obtained, using least mean square approximation the mean values of all columns except for a pre-selected number of columns in the immediate vicinity of the bad pixel column (shown as columns C−2, C−1, C0, C+1, and C+2), are fitted into a first order polynomial, represented in the figure as baseline 10. The number of columns omitted from the calculation depends on the number of columns effected by the bad pixel column on either side of the bad pixel column. This number is typically between 1 and 5, and can be determined by observation when the bad column is first identified.

The bad pixel column correction process next performs the following two calculations in blocks (7) and (10). Optional steps (8) and (9) will be discussed later in this description. Let the array X(I,J) represent the pixels values in the buffer, with I from −N to +N and J from 0 to L where L is equal to R1e−R1s. As discussed, the buffered array was divided into a plurality of identical sub-arrays along J and for each sub-array there was calculated the mean value in each column of the sub-array. For each sub-array there is now created a one dimensional sub-array of mean values A(I, JA) where JA is the sub-array number. Next, without using the values for the bad source column, and the values of the effected columns on either side of the bad column, (which is a predetermined number) the remaining mean values for each sub-array are fitted into a straight line, $LINE_A(I,JA)$ which form a baseline for each of the sub-arrays, step (7).

$LINE_A(I,JA)=C+G*I$, for I=−N to +N. C and G are chosen so as to produce the least mean square error between baseline, $LINE_A(I,JA)$, and A(I, JA) for each I, excluding the excluded pixels in the excluded columns. The distortion coefficient D(I, JA) for sub-array JA is obtained (8) from:

$D(I,J)=A(I,JA)/LINE_A(I,JA)$. for all bad pixel columns.

The distortion coefficients may be passed through a low pass filter to eliminate high frequency contents in the J direction (11) and applied to the bad pixel column pixels (12) to provide replacement pixel values which are then used to replace the values of the defective pixels (13). New pixels may be calculated by dividing the old pixel value by the distortion coefficient for the column in which the pixel is located. If there is another bad pixel column, the process repeats for step (4), if not, the image display process continues.

The following numerical example will next be used to illustrate the correction process for a bad pixel line consisting of 9 pixels in rows R1–R9 and in column C5. All values shown have been selected only for the purpose of illustration and do not correspond to any recorded actual data. The numerical values in the tables represent a fictitious digital value corresponding to a display density resulting from a fictitious exposure of the detector to imaging radiation. As shown in table 1 it is assumed that the distortion only extends to one adjacent column on either side of the bad column. Further more only three good columns on either side of the bad column will be used in the derivation of the correction factors for generating replacement pixel values for the affected columns. In its actual implementation of this invention in a medical diagnostic environment, typical distortion has been found to extend to at least three columns on either side of the bad column, and, as stated above, the preferred pixel neighborhood used usually extends to the $16^{th}$ column on either side of the bad column.

TABLE 1

|    | C1 | C2 | C3 | C4 | C5 | C6 | C7 | C8 | C9 |
|----|----|----|----|----|----|----|----|----|-----|
| R1 | 26 | 26 | 24 | 32 | 45 | 37 | 24 | 25 | 26 |
| R2 | 25 | 27 | 25 | 33 | 46 | 36 | 24 | 24 | 25 |
| R3 | 26 | 25 | 25 | 33 | 47 | 37 | 25 | 26 | 24 |
| R4 | 24 | 27 | 23 | 35 | 50 | 36 | 26 | 25 | 26 |
| R5 | 25 | 26 | 25 | 33 | 48 | 38 | 25 | 23 | 24 |
| R6 | 24 | 27 | 26 | 34 | 47 | 37 | 24 | 24 | 23 |
| R7 | 25 | 26 | 24 | 36 | 48 | 36 | 25 | 23 | 26 |
| R8 | 25 | 25 | 23 | 36 | 47 | 35 | 24 | 26 | 26 |
| R9 | 24 | 26 | 23 | 37 | 48 | 34 | 23 | 26 | 24 |

The first step consists of dividing the data into sub-arrays, comprising small, overlapping blocks of rows and columns, as shown below. Again the block size has been selected for illustration purposes and in order to keep the computations to a minimum. Preferably the blocks extend to six rows with two overlapping rows.

|    | C1 | C2 | C3 | C4 | C5 | C6 | C7 | C8 | C9 |
|----|----|----|----|----|----|----|----|----|----|
|    |    |    |    | First sub-array |    |    |    |    |    |
| R1 | 26 | 26 | 24 | 32 | 45 | 37 | 24 | 25 | 26 |
| R2 | 25 | 27 | 25 | 33 | 46 | 36 | 24 | 24 | 25 |
| R3 | 26 | 25 | 25 | 33 | 47 | 37 | 25 | 26 | 24 |
| R4 | 24 | 27 | 23 | 35 | 50 | 36 | 26 | 25 | 26 |
|    |    |    | Second sub-array, one overlapping row |    |    |    |    |    |    |
| R4 | 24 | 27 | 23 | 35 | 50 | 36 | 26 | 25 | 26 |
| R5 | 25 | 26 | 25 | 33 | 48 | 38 | 25 | 23 | 24 |
| R6 | 24 | 27 | 26 | 34 | 47 | 37 | 24 | 24 | 23 |
| R7 | 25 | 26 | 24 | 36 | 48 | 36 | 25 | 23 | 26 |
|    |    |    | Third sub-array, one overlapping row |    |    |    |    |    |    |
| R7 | 25 | 26 | 24 | 36 | 48 | 36 | 25 | 23 | 26 |
| R8 | 25 | 25 | 23 | 36 | 47 | 35 | 24 | 26 | 26 |
| R9 | 24 | 26 | 23 | 37 | 48 | 34 | 23 | 26 | 24 |

Next, we calculate the average value B-mean, for each column of each sub-array.

|         | C1 | C2 | C3 | C4 | C5 | C6 | C7 | C8 | C9 |
|---------|----|----|----|----|----|----|----|----|----|
|         |    |    |    | First sub-array |    |    |    |    |    |
| B1-mean:| 25.25 | 26.25 | 24.25 | 33.25 | 47 | 36.5 | 24.75 | 25 | 25.25 |
|         |    |    |    | Second sub-array |    |    |    |    |    |
| B2-mean:| 24.25 | 26.5 | 24.5 | 34.5 | 48.25 | 36.75 | 25 | 23.75 | 24.75 |
|         |    |    |    | Third sub-array |    |    |    |    |    |
| B3-mean:| 24.67 | 25.67 | 23.34 | 36.67 | 47.67 | 35 | 24 | 25 | 25.33 |

Next, we ignore values for bad column and adjacent columns on either side and we calculate a best linear mean square curve fit for each of the remaining B-mean values. The following numerical example illustrates the first sub-array calculation of the least square line fit.

Assign the I variable as the location for each column with the zero axis on the bad column. Applying this to the first block mean values we have:

|               | C1 | C2 | C3 |   |   |   | C7 | C8 | C9 |
|---------------|----|----|----|---|---|---|----|----|----|
| B1-mean value | 25.25 | 26.25 | 24.25 | — | — | — | 24.75 | 25 | 25.25 |
| I value       | -4 | -3 | -2 | 1 | 0 | 1 | 2 | 3 | 4 |

A straight line can be expressed as $$\text{LINE}_A(I, JA) = E + G*I \text{ for } I = -4, -3, \ldots 0 \ldots 4. \quad (1)$$

where E is a constant, and G is the slope factor of the line.
E and G are calculated as follows:

$E = (B1C1 + B1C2 + B1C3 + B1C7 + B1C8 + B1C9)/6 = (25.25 + 26.25 + \ldots + 25.25)/6$ and $E = 25.125$.

$G = (B1C1*(-4) + B1C2*(-3) + B1C3*(-2) + B1C7*2 + B1C8*3 + B1C9*4)/(4*4 + 3*3 + 2*2 + 2*2 + 3*3 + 4*4) = (25.25*(-4) + 26.25*(-3) + \ldots + 25.25*4) = 582.75/58$
thus $G = -0.047413$.

With E and G calculated, the baseline values at (C1, C2, . . . C9) can be found from equation (1) which becomes:

$$\text{LINE}_A(I, JA) = 25.125 - 0.047413 * I \quad (1)$$

At C1, I=−4 and $\text{LINE}_A(-4, \text{Block1}) = 25.125 - 0.047413*(-4) = 25.3146$ At C2, I=−3 and $\text{LINE}_A(-3, \text{Block1}) = 25.125 - 0.047413*(-3) = 25.2672$ At C9 I=+4 and $\text{LINE}_A(+14, \text{Block1}) = 25.125 - 0.047413*4 = 24.935$.

We now have the B1-mean data and its fitted baseline values for each of the columns. Values have been rounded to two significant figures.

|          | C1 | C2 | C3 | C4 | C5 | C6 | C7 | C8 | C9 |
|----------|----|----|----|----|----|----|----|----|----|
| B1-mean  | 25.25 | 26.2 | 24.2 | 33.25 | 47 | 36.5 | 24.75 | 25 | 25.25 |
| Baseline | 25.32 | 25.26 | 25.22 | 25.17 | 25.13 | 25.08 | 25.03 | 24.98 | 24.95 |

Next, the distortion coefficients D1(I) for the omitted columns in sub-array I are calculated as:

|    | C4 | C5 | C6 |
|----|----|----|----|
| D1 | 33.25/25.17 = 1.32 | 47/25.13 = 1.9 | 36.5/25.08 = 1.46 |

We next apply the distortion coefficient D1 to each row of the omitted columns to generate the following replacement pixel values:

|    | C4            | C5            | C6            |
|----|---------------|---------------|---------------|
| R1 | 32/1.32 = 24.24 | 45/1.9 = 23.68 | 37/1.46 = 25.34 |
| R2 | 33/1.32 = 25.0  | 46/1.9 = 24.21 | 36/1.46 = 24.66 |
| R3 | 33/1.32 = 25.0  | 47/1.9 = 24.74 | 37/1.46 = 25.34 |
| R4 | 35/1.32 = 26.5  | 50/1.9 = 26.32 | 36/1.46 = 24.66 |

The process is repeated for the next sub-array until all sub-arrays have been processed. Because there is overlapping of certain rows in each sub-array, two values may be obtained for each of the overlapping rows. In one embodiment of this invention, the second sub-array value for the overlapping rows is discarded. Alternatively, the two values may be averaged and the average value used, or the first sub-array value may be always discarded and the second sub-array value used. In most instances, the choice of overlapping row values will not significantly effect the image representation in that area because the difference in calculated values between subarrays is, for practical purposes, minimal. However, in cases where the density gradient in the image area where the two sub-arrays are located changes rapidly, it is preferred to interpolate the overlapping row value from the two row values calculated for the two sub-arrays. Most often a simple arithmetic average will provide adequate results.

The process is repeated for all sub-arrays and the calculated values for columns C4 through C6 are used to replace the original values in table 1 and generate the display value table 2.

TABLE 2

|    | C1 | C2 | C3 | C4 | C5 | C6 | C7 | C8 | C9 |
|----|----|----|----|----|----|----|----|----|----|
| R1 | 26 | 26 | 24 | 24 | 24 | 25 | 24 | 25 | 26 |
| R2 | 25 | 27 | 25 | 25 | 24 | 25 | 24 | 24 | 25 |
| R3 | 26 | 25 | 25 | 25 | 25 | 25 | 25 | 26 | 24 |
| R4 | 24 | 27 | 23 | 26 | 26 | 25 | 26 | 25 | 26 |
| R5 | 25 | 26 | 25 | 25 | 25 | 26 | 25 | 23 | 24 |

TABLE 2-continued

|    | C1 | C2 | C3 | C4 | C5 | C6 | C7 | C8 | C9 |
|----|----|----|----|----|----|----|----|----|----|
| R6 | 24 | 27 | 26 | 26 | 25 | 25 | 24 | 24 | 23 |
| R7 | 25 | 26 | 24 | 27 | 25 | 24 | 25 | 23 | 26 |
| R8 | 25 | 25 | 23 | 25 | 24 | 25 | 24 | 26 | 26 |
| R9 | 24 | 26 | 23 | 26 | 25 | 24 | 23 | 26 | 24 |

In a preferred embodiment of the invention, the correction process includes an additional series of steps intended to identify how good is the first order approximation used to derive the distortion coefficients, by calculating the deviation of the mean values from the baseline values. This may be done by calculating a normalized approximation indicator, App(JA), preferably in step (8) of FIG. 2.

$$App(JA)=[\Sigma((LINE(I,JA)-A(I,JA))*(LINE(I,JA)-A(I,JA)))]^{1/2}/[\Sigma A(I,JA)]^{1/2} \quad (3)$$

For I from −N to −(First good column) and I from +(First good column) to +N and for each JA.

The resulting approximation indicators for all sub-arrays are compared in step (9) and in the sub-arrays where the indicators have a value exceeding a predetermined number, the distortion coefficients are replaced by coefficients extrapolated from the distortion coefficients of adjacent arrays having acceptable distortion coefficients. In an alternative approach, the approximation indicators are divided into two halves. All distortion coefficients corresponding to arrays having indicators in the higher half are discarded and replaced by interpolation from coefficients from the remaining arrays.

Interpolation may again be linear interpolation, where $$D(I,JA)=f*D(Is,JA)+(1.0-f)*D(Ie,JA)$$

where $D(I,JA)$ is the replacement distortion coefficient and $D(Is,JA)$ and $D(Ie,JA)$ are the two adjacent valid distortion coefficients. The interpolation factor f varies between 0–1.

Applying the above approximation indicator calculation to the illustrating example used above we proceed as follows:

|        | C1    | C2    | C3    | C4    | C5    | C6    | C7    | C8    | C9    |
|--------|-------|-------|-------|-------|-------|-------|-------|-------|-------|
|        |       |       |       | First block |  |       |       |       |       |
| B1mean | 25.25 | 26.2  | 24.2  | 33.25 | 47    | 36.5  | 24.75 | 25    | 25.25 |
|        |       |       |       | Second block |  |       |       |       |       |
| B2mean: | 24.25 | 26.5  | 24.5  | 34.5  | 48.25 | 36.75 | 25    | 23.75 | 24.75 |
|        |       |       |       | Third block |  |       |       |       |       |
| B3mean: | 24.67 | 25.67 | 23.34 | 36.67 | 47.67 | 35    | 24    | 25    | 25.33 |

For each block we calculate the baseline, LINE (I, JA) values for each column and the average (B1mean/6) of the block mean values. This produces the following values:

|            | C1      | C2     | C3    | C4      | C5     | C6     | C7    | C8    | C9     |
|------------|---------|--------|-------|---------|--------|--------|-------|-------|--------|
| B1mean     | 25.25   | 26.2   | 24.2  |         |        |        | 24.75 | 25    | 25.25  |
| B1 Average | 25.125  |        |       |         |        |        |       |       |        |
| Line (I, JA1) | 25.3146 | 25.267 | 25.22 | 25.1723 | 25.125 | 25.077 | 25.03 | 24.98 | 24.935 |

-continued

|   | C1 | C2 | C3 | C4 | C5 | C6 | C7 | C8 | C9 |
|---|---|---|---|---|---|---|---|---|---|
| B2mean | 24.25 | 26.5 | 24.5 | | | | 25 | 23.75 | 24.75 |
| B2 Average | 25.708 | | | | | | | | |
| Line (I, JA2) | 24.23 | 24.462 | 24.544 | 24.626 | 24.708 | 24.79 | 24.872 | 24.954 | 25.036 |
| B3mean | 24.67 | 25.67 | 23.34 | | | | 24 | 25 | 25.33 |
| B3 Average | 24.67 | | | | | | | | |
| Line (I, JA3) | 24.53 | 24.56 | 24.59 | 24.62 | 24.67 | 24.70 | 24.73 | 24.77 | 24.80 |

For Block 1 the error square is:
$(25.25-25.3146)^2+(26.25-25.267)^2+(24.25-25.22)^2+(24.75-25.03)^2+(25-24.98)^2+(25.25-24.935)^2=2.089$ and the square root of the error is $(2.089/6)^{1/2}=0.59$. The root mean square is next normalized by division by the square root of the B1 average, $25.125^{1/2}$, which equals 5.012 to derive the approximation indicator $App_1=0.1177$. Using the same process steps, $App_2=0.1329$ and $App_3=0.1525$. $App_3$ is substantially larger than $App_1$ raising a question whether the process is masking actual image information. To test this we find the half point for the App indicators. The half point is 0.1344. Next we discard the distortion coefficients calculated for block 3 and replace them by extrapolating from the preceding coefficients.

In this example, D1 for C4, C5, and C6 was calculated as D1C4=1.37, D1C5=1.92 and D1C6=1.47. D2 for C4, C5, and C6 calculates as D2C4=1.31, D2C5=1.90, and D2C6=1.47. From these, using linear interpolation we calculate the following D3 values: D3C4=1.15, D3C5=1.88 and D3C6=1.47. With these corrections in place the original table 1 becomes:

TABLE 3

|    | C1 | C2 | C3 | C4 | C5 | C6 | C7 | C8 | C9 |
|----|----|----|----|----|----|----|----|----|----|
| R1 | 26 | 26 | 24 | 24 | 24 | 25 | 24 | 25 | 26 |
| R2 | 25 | 27 | 25 | 25 | 24 | 25 | 24 | 24 | 25 |
| R3 | 26 | 25 | 25 | 25 | 25 | 25 | 25 | 26 | 24 |
| R4 | 24 | 27 | 23 | 26 | 26 | 25 | 26 | 25 | 26 |
| R5 | 25 | 26 | 25 | 25 | 25 | 26 | 25 | 23 | 24 |
| R6 | 24 | 27 | 26 | 26 | 25 | 25 | 24 | 24 | 23 |
| R7 | 25 | 26 | 24 | 27 | 25 | 24 | 25 | 23 | 26 |
| R8 | 25 | 25 | 23 | 31 | 25 | 24 | 24 | 26 | 26 |
| R9 | 24 | 26 | 23 | 32 | 26 | 23 | 23 | 26 | 24 |

The invention is best implemented through a properly programmed computer instructed to perform the described functions. Such program may be embodied in ROM (read only memory), RAM (random access memory, or a storage device such as magnetic storage medium or CD ROM disk. Both the means for writing and reading the program from such media and for implementing the instructions contained therein are well known in the art and need no further elaboration.

As each replacement pixel value is calculated, the new pixel value may be stored in a memory containing the full pixel values of the captured image. Once the first defective pixel column has been corrected the program performs the same operations to the second line in the bad pixel column file and so on until all pixel column defects have been processed. The operations involved are simple and can be performed rapidly. Thus, if desired, the original raw data may be kept intact and the above operations performed each time, the data is prepared for display.

In case where there are two or more adjacent bad pixel columns it is preferred according to the present invention to select a number of columns adjacent to the leftmost of the bad pixel lines and an equal number of columns adjacent to the rightmost of the bad pixel lines and then proceed as before, rather than treating each bad pixel line individually in turn.

The invention has been described with reference to a particular type of detector and certain specific numerical values. The detector used in the aforementioned description of this invention is a radiographic detector capable of capturing medical diagnostic quality images which are, following image processing including the corrections described in this invention, displayed in either hard copy format or soft display. It may be a single unit or may comprise a plurality of smaller detectors tiled to produce a detector sufficiently large for medical radiography.

Specific algorithms have been applied in calculating the base values, however this was done by way of explanation rather than limitation. For instance, while the least square method of fitting a first order polynomial appears usually adequate for a best fit approximation the use of higher order polynomials to provide more accurate baseline value calculations may be used and is within the scope of the present invention. Similarly, while linear interpolation has been used to demonstrate the calculation of replacement distortion coefficients, other more complex interpolation methods may be used for these calculations. Such mathematical techniques are well known to the practitioners of image restoration and noise reduction and are within the scope of my invention, in which I claim:

What is claimed is:

1. In a radiation detector comprising a plurality of radiation sensing picture elements (Pixels) arrayed along rows and columns, a method for correcting inaccurate pixel values from a bad pixel column of linearly arrayed plurality of adjacent pixels for use in displaying an image of radiation sensed by the sensors, the method comprising:

A) identifying said plurality of pixels forming the bad pixel column and storing the location of said pixels in a memory;

B) selecting a plurality of adjacent co-extensive columns of pixels, on either side of said bad pixel column and together with the bad pixel column pixels forming an array of selected first pixel values;

C) calculating a mean column value for each column of pixel values in each column of the array of selected first values;

D) ignoring the bad pixel column mean value, calculate a set of base line values for each column in the array except for said bad pixel column;

E) from the calculated base line values interpolating an interpolated base line value for the bad pixel column;

F) calculating a distortion correction coefficient equal to the ratio of the mean pixel value in the bad pixel column and the interpolated base line value for said column; and G) applying the distortion coefficient to the bad pixel column values to derive corrected pixel values for each of the pixels in the bad pixel column.

2. The method according to claim 1 wherein the step of calculating the base line values comprises fitting the mean values of the columns, except for the bad pixel column, into a first order polynomial using least mean square approximation.

3. In a radiation detector comprising a plurality of radiation sensing picture elements (Pixels) arrayed along rows and columns, a method for correcting inaccurate pixel values from a bad pixel column of linearly arrayed plurality of adjacent pixels for use in displaying an image of radiation sensed by the sensors, the method comprising:

A) identifying said plurality of pixels forming the bad pixel column and storing the location of said pixels in a memory;

B) selecting a plurality of adjacent co-extensive columns of pixels, on either side of said bad pixel column and together with the bad pixel column pixels forming a first array of pixel values;

C) dividing said first array of pixel values into a plurality of sub-arrays, each sub-array comprising a same number of columns as the first array and a number of rows lesser than the total number of rows in the first array;

D) calculating a mean column value for each column of pixel values in each column of a first sub-array of said plurality of sub-arrays;

E) ignoring the bad pixel column mean value in said first sub-array, calculate a set of first base line values for each column in the first sub-array except for said bad pixel first sub-array column, F) from the calculated first base line values interpolating an interpolated first base line value for the first sub-array bad pixel column;

G) calculating a distortion correction coefficient for the first sub-array, equal to the ratio of the mean pixel value in the first sub-array bad pixel column and the interpolated first sub-array base line value for said column;

H) applying the distortion coefficient to the first sub-array bad pixel column values in the first sub-array to derive corrected first sub-array pixel values for each of the pixels in the bad pixel column; and I) replacing the bad pixel values in the bad pixel column by the corrected pixel values.

4. The process according to claim 3 further comprising following step (I), repeating steps (D) through (I) for each of the plurality of sub-arrays.

5. The process according to claim 3 further comprising the step of displaying said image.

6. The process according to claim 3 wherein in step (B), adjacent sub-arrays include an overlapping row.

7. The process according to claim 3 wherein in steps (E) through (I) the ignored column pixel comprises an additional pixel column adjacent the bad pixel column.

8. The process according to claim 3 wherein in steps (E) through (I) the ignored pixel column comprises an additional pixel column adjacent either side of the bad pixel column.

9. The process according to claim 3 wherein in step (B) the sub-arrays each comprise between 4 and 8 pixel rows.

10. The process according to claim 3 wherein following step (F) there is calculated an approximation indicator representing a deviation between the base values and the mean values for each sub-array and wherein after all approximation indicators for all sub-arrays have been calculated all distortion coefficients in all sub-arrays having an approximation indicator greater than half the approximation indicators of all sub-arrays are replaced by new distortion coefficients extrapolated from adjacent distortion coefficients in sub-arrays having an approximation indicator that is equal to or less than half the approximation factors for all the sub-arrays in step (H).

11. The process according to claim 10 wherein the approximation indicator is equal to the square root of the sum of the squares of the difference between the mean values and the baseline values for each of the pixel columns except for the bad pixel column in each sub-array divided by the number of such columns in the sub-array.

12. The process according to claim 3 wherein the radiation detector is a radiographic detector and the pixels represent pixels of a medical diagnostic radiogram.

13. The process according to claim 3 wherein the radiographic detector comprises a plurality of smaller detectors tiled to form said detector.

14. The process according to claim 3 wherein the adjacent bad pixels each includes a switching transistor having a source electrode and all said source electrodes are connected to a common pixel column conductor.

15. A program storage device readable by a machine, tangibly embodying a program of instructions executable by the machine to perform the method steps for correcting inaccurate pixel values from a bad pixel column of linearly arrayed plurality of adjacent picture elements (Pixels) in following radiation exposure of a radiation detector comprising a plurality of radiation sensors each sensor representing a pixel, the pixels arrayed along rows and columns, wherein said corrected pixel values are used in displaying an image of said radiation exposure of the detector, the method comprising:

A) identifying said plurality of pixels forming the bad pixel column and storing the location of said pixels in a memory;

B) selecting a plurality of adjacent co-extensive columns of pixels, on either side of said bad pixel column and together with the bad pixel column pixels forming a first array of pixel values;

C) dividing said first array of pixel values into a plurality of sub-arrays, each sub-array comprising a same number of columns as the first array and a number of rows lesser than the total number of rows in the first array;

D) calculating a mean column value for each column of pixel values in each column of a first sub-array of said plurality of sub-arrays;

E) ignoring the bad pixel column mean value in said first sub-array, calculate a set of first base line values for each column in the first sub-array except for said bad pixel first sub-array column;

F) from the calculated first base line values interpolating an interpolated first base line value for the first sub-array bad pixel column;

G) calculating a distortion correction coefficient for the first sub-array, equal to the ratio of the mean pixel value in the first sub-array bad pixel column and the interpolated first sub-array base line value for said column;

H) applying the distortion coefficient to the first sub-array bad pixel column values in the first sub-array to derive corrected first sub-array pixel values for each of the pixels in the bad pixel column; and I) replacing the bad pixel values in the bad pixel column by the corrected pixel values.

16. The programmable device according to claim 12 wherein the process further comprises following step (F) calculating an approximation indicator representing a deviation between the base values and the mean values for each sub-array and wherein after all approximation indicators for all sub-arrays have been calculated all distortion coefficients in all sub-arrays having an approximation indicator greater than half the approximation indicators of all sub-arrays are replaced by new distortion coefficients extrapolated from adjacent distortion coefficients in sub-arrays having an approximation indicator that is equal to or less than half the approximation indicators for all the sub-arrays in step (H).

17. The process according to claim 16 wherein the approximation indicator is equal to the square root of the sum of the squares of the difference between the mean values from the base values for each of the pixel columns except for the bad pixel column in each sub-array divided by the number of such columns in the sub-array.

18. An article of manufacture comprising:

a computer useable medium having computer readable program code means embodied therein causing the correction of inaccurate pixel values from a bad pixel column of linearly arrayed plurality of adjacent picture elements (Pixels) in a radiation detector comprising a plurality of radiation sensors each sensor representing a pixel, the pixels arrayed along rows and columns, the computer readable means in said article of manufacture comprising:

A) identifying said plurality of pixels forming the bad pixel column and storing the location of said pixels in a memory;

B) selecting a plurality of adjacent co-extensive columns of pixels, on either side of said bad pixel column and together with the bad pixel column pixels forming a first array of pixel values;

C) dividing said first array of pixel values into a plurality of sub-arrays, each sub-array comprising a same number of columns as the first array and a number of rows lesser than the total number of rows in the first array;

D) calculating a mean column value for each column of pixel values in each column of a first sub-array of said plurality of sub-arrays;

E) ignoring the bad pixel column mean value in said first sub-array, calculate a set of first base line values for each column in the first sub-array except for said bad pixel first sub-array column;

F) from the calculated first base line values interpolating an interpolated first base line value for the first sub-array bad pixel column;

G) calculating a distortion correction coefficient for the first sub-array, equal to the ratio of the mean pixel value in the first sub-array bad pixel column and the interpolated first sub-array base line value for said column;

H) applying the distortion coefficient to the first sub-array bad pixel column values in the first sub-array to derive corrected first sub-array pixel values for each of the pixels in the bad pixel column; and I) replacing the bad pixel values in the bad pixel column by the corrected pixel values.

\* \* \* \* \*